United States Patent
Dirauf et al.

(10) Patent No.: US 9,011,002 B2
(45) Date of Patent: Apr. 21, 2015

(54) RADIATION GENERATION UNIT

(75) Inventors: Franz Dirauf, Ebensfeld (DE); Franz Fadler, Hetzles (DE); Gernot Schimetta, München (DE); Stefan Setzer, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 404 days.

(21) Appl. No.: 13/218,322

(22) Filed: Aug. 25, 2011

(65) Prior Publication Data

US 2012/0213334 A1    Aug. 23, 2012

(30) Foreign Application Priority Data

Aug. 26, 2010   (DE) .................. 10 2010 035 538

(51) Int. Cl.
*H05G 1/02* (2006.01)
*A61N 5/10* (2006.01)
*A61N 5/01* (2006.01)

(52) U.S. Cl.
CPC .................. *A61N 5/1081* (2013.01); *A61N 5/01* (2013.01)

(58) Field of Classification Search
CPC ............ G21K 5/00; G21K 5/04; G21K 5/08; G21K 5/10; A61L 2/08; A61N 5/10; A61N 5/1077; H05G 1/02; H05G 1/04; H05G 1/06; A61B 6/4405
USPC ....................... 378/64, 65, 193, 194, 197, 198
See application file for complete search history.

(56) References Cited

U.S. PATENT DOCUMENTS

| | | | | |
|---|---|---|---|---|
| 2,668,912 A | * | 2/1954 | Goldfield et al. | 378/190 |
| 5,751,781 A | | 5/1998 | Brown et al. | |
| 6,839,404 B2 | | 1/2005 | Clark et al. | |
| 7,759,883 B2 | * | 7/2010 | Gatto | 315/505 |
| 8,050,384 B2 | * | 11/2011 | Carol et al. | 378/65 |
| 8,632,246 B2 | * | 1/2014 | Dirauf et al. | 378/197 |
| 2008/0303457 A1 | | 12/2008 | Maltz | |
| 2009/0097614 A1 | | 4/2009 | Bergfjord et al. | |

FOREIGN PATENT DOCUMENTS

| | | |
|---|---|---|
| EP | 0 919 186 A2 | 6/1999 |
| EP | 1 317 944 A1 | 6/2003 |
| GB | 2 382 512 A | 5/2003 |

OTHER PUBLICATIONS

German Office Action dated Jun. 30, 2011 for corresponding German Patent Application No. DE 10 2010 035 538.0 with English translation.

* cited by examiner

*Primary Examiner* — Jurie Yun
(74) *Attorney, Agent, or Firm* — Lempia Summerfield Katz LLC (57) ABSTRACT

The present embodiments relate to a radiation generation unit for a therapy system. The radiation generation unit has a radiation source and support components for the radiation source. The radiation generation unit includes a power source and has a mechanical interface, with which the radiation generation unit may be attached to a stand. Degrees of freedom of movement may easily be implemented using a corresponding movement of the radiation generation unit.

18 Claims, 7 Drawing Sheets

FIG 1

PRIOR ART

FIG 2

PRIOR ART

FIG 3

PRIOR ART

RADIATION GENERATION UNIT

This application claims the benefit of DE 10 2010 035 538.0, filed on Aug. 26, 2010.

BACKGROUND

The present embodiments relate to a radiation generation unit for a therapy system.

Radiotherapy is a well-established medical method for eliminating damaged tissue. High-energy electromagnetic radiation (e.g., in the MV range) may be used. This electromagnetic radiation may be generated with the aid of electrons that are accelerated by a linear accelerator and hit a target (e.g., a tungsten target) at high speed, with electromagnetic radiation being generated in the context of the scatter processes. This radiation is focused and directed at an isocenter, which corresponds to a location of damaged tissue.

Figure 1:
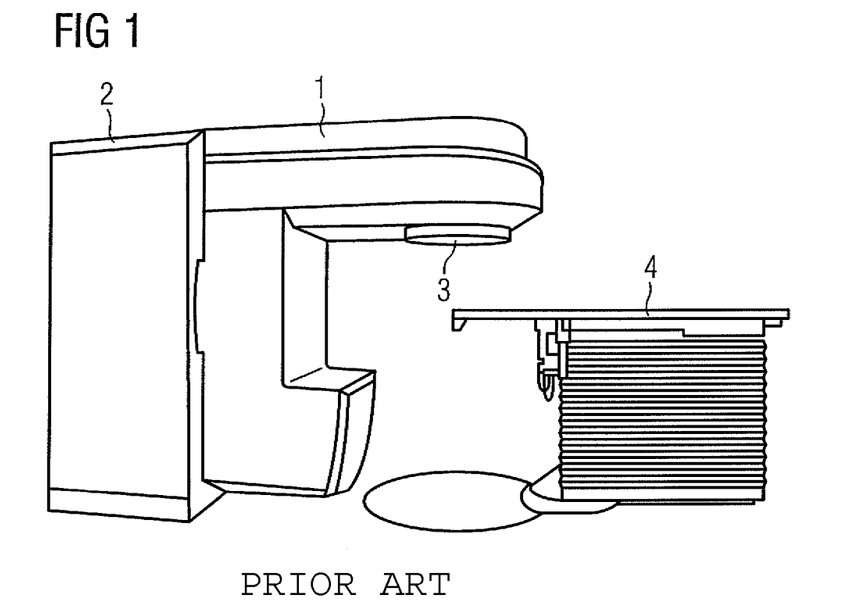
FIG. 1 shows a therapy system.
Figure 2:
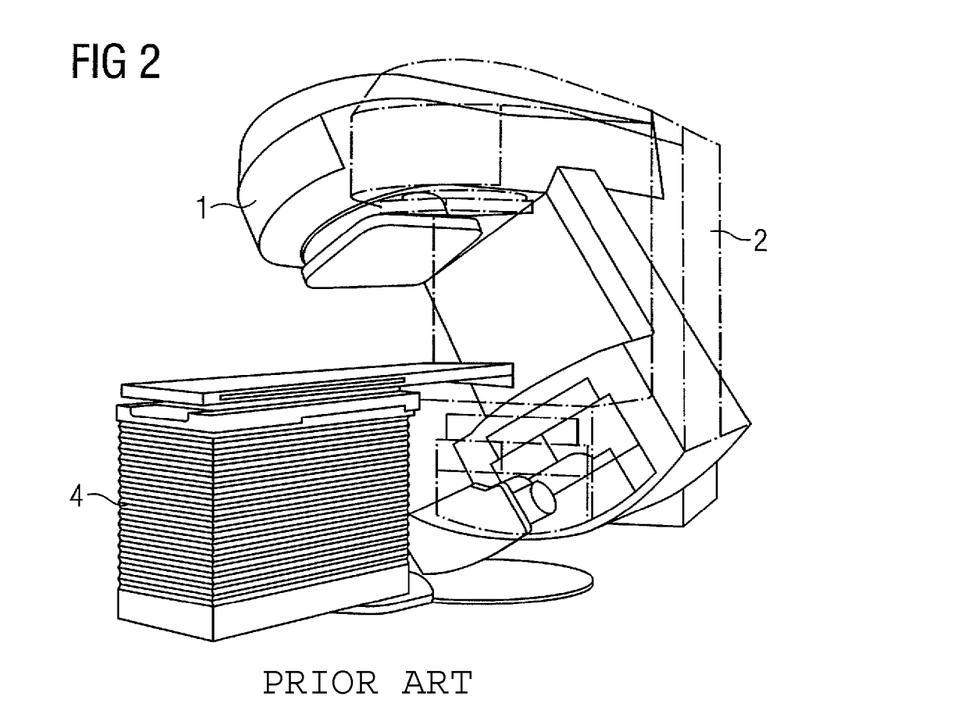
FIG. 2 shows a therapy system when tilted.
Figure 3:
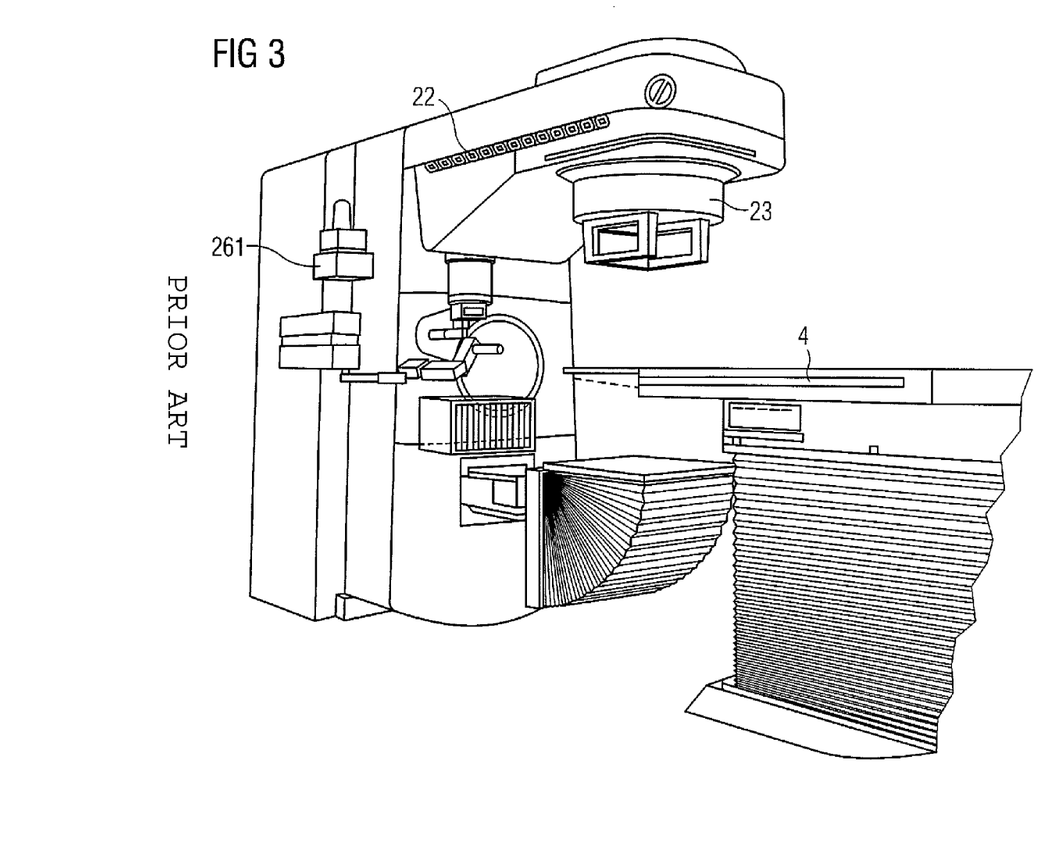
FIG. 3 shows a therapy system with some components.

FIG. 1, FIG. 2 and FIG. 3 show a known therapy system. The therapy system is, for example, also described in U.S. Pat. No. 6,839,404 B2.

In FIG. 3, relevant components of the therapy system are shown. A high-frequency power source 261 and a high-voltage modulator are accommodated in a static part or a stand 2. The high frequency (HF) power is conveyed to a rotating gantry via a hollow conductor with rotary feedthrough (e.g., a rotary joint). In addition to a linear accelerator tube 22, a 4-port circulator, an electron injector (neither of which are shown) and a multileaf collimator 23 are also disposed there.

SUMMARY AND DESCRIPTION

A need exists for more flexible irradiation facilities that permit simpler configuration of the irradiation facility, simpler maintenance and more flexibility and degrees of freedom during irradiation.

The present embodiments may obviate one or more of the drawbacks or limitations in the related art. For example, a more flexible irradiation facility may be provided.

In one embodiment, a radiation generation unit (e.g., an irradiator unit) for a therapy facility (e.g., a therapy system) that includes a radiation source and support components for the radiation source is provided. The radiation source is, for example, designed for generating a therapy beam (e.g., a beam suitable for destroying diseased tissue). The support components include an energy generation unit. By integrating radiation source and energy generation in a single unit, the radiation source and the energy generation unit may be positioned jointly. For example, the energy generation unit may be moved together with the radiation source (e.g., no longer disposed in a static part). An interface between the radiation source and the energy generation unit becomes easier to implement, and a more flexible concept permits an irradiation facility with more degrees of freedom.

In one embodiment, the radiation generation unit essentially has a linear, elongated structure or shape that is achieved in that the components of the radiation generation unit are disposed behind one another. the radiation generation unit has one or more mechanical interfaces, with which the radiation generation unit may be attached to a stand. This radiation generation unit is relatively compact and has a clearly defined interface or a plurality of defined interfaces, with which the radiation generation unit may be suspended. In one embodiment, the radiation generation unit includes or contains all components for generating a therapy beam. The components for generating the therapy beam are integrated as compactly as possible. The result is a separation of the radiation generation unit from the mechanical structure for positioning. This has the following advantages:

The beam generation unit may be combined with different kinematic structures with relatively little effort, so that easily adapted device variants may be implemented from a modular system for different areas of application.

The manufacture, testing, logistics and installation of beam generation unit and mechanism are decoupled. The processes may be optimized, saving time and costs. Only the compact beam generation unit may be tested and adjusted in the radiation bunker, while the mechanical structure already installed in parallel in the clinic may be taken into operation.

The arrangement of the radiation generation components in the compact unit permits far more degrees of freedom for positioning relative to the patient, so that new methods and sequences are possible in radiotherapy (e.g., methods and sequences that in the case of the known devices with a single rotational axis about a fixed isocenter are ruled out). For example, the following are possible: a variable isocenter, a variable distance between the radiation source and the isocenter, a variable angle of incidence to the isocenter in all spatial directions, and user-defined trajectories instead of circular paths.

For renewals, upgrades and larger repairs, the beam generation unit may be exchanged in the clinic in a very short time compared to conventional devices. For example, a replacement unit may also be installed during the repair time, thereby giving virtually no downtimes in the hospital.

In one embodiment of the radiation generation unit, the mechanical interface may be disposed in a central area of the elongated structure. This has the advantage that the weights on both sides of the mechanical interface at least partially offset one another (e.g., the mechanical stress is reduced). The mechanical interface may, for example, include a vertically oriented surface, with which the radiation generation unit is attached to a slide or to another structure. The mechanical interface is configured for attachment such that the radiation generation unit may be demounted or removed again. For example, the radiation generation unit may be fixed using a screw connection.

The radiation generation unit may include the following components: a linear accelerator for electrons (e.g., for higher energies, a long tube with a deflection magnet or a short tube in a perpendicular arrangement without the deflection magnet may be used as the linear accelerator); a high frequency (HF) power source for the linear accelerator (e.g., a magnetron); a high-voltage supply for an HF power source (e.g., a modulator); targets and filters for a radiation dosimetry system for measuring the generated radiation; collimators for beam formation (e.g., a multileaf collimator); power supplies; control and monitoring electronics; and cooling and other infrastructure.

DETAILED DESCRIPTION OF THE DRAWINGS

FIG. 1 and FIG. 2 show a therapy system, in which a degree of freedom (e.g., rotation) of a radiation source 3 is provided. Further degrees of freedom are achieved by patient positioning using a patient table 4.

FIG. 3 shows components for generating radiation in a conventional therapy system.

Figure 4:
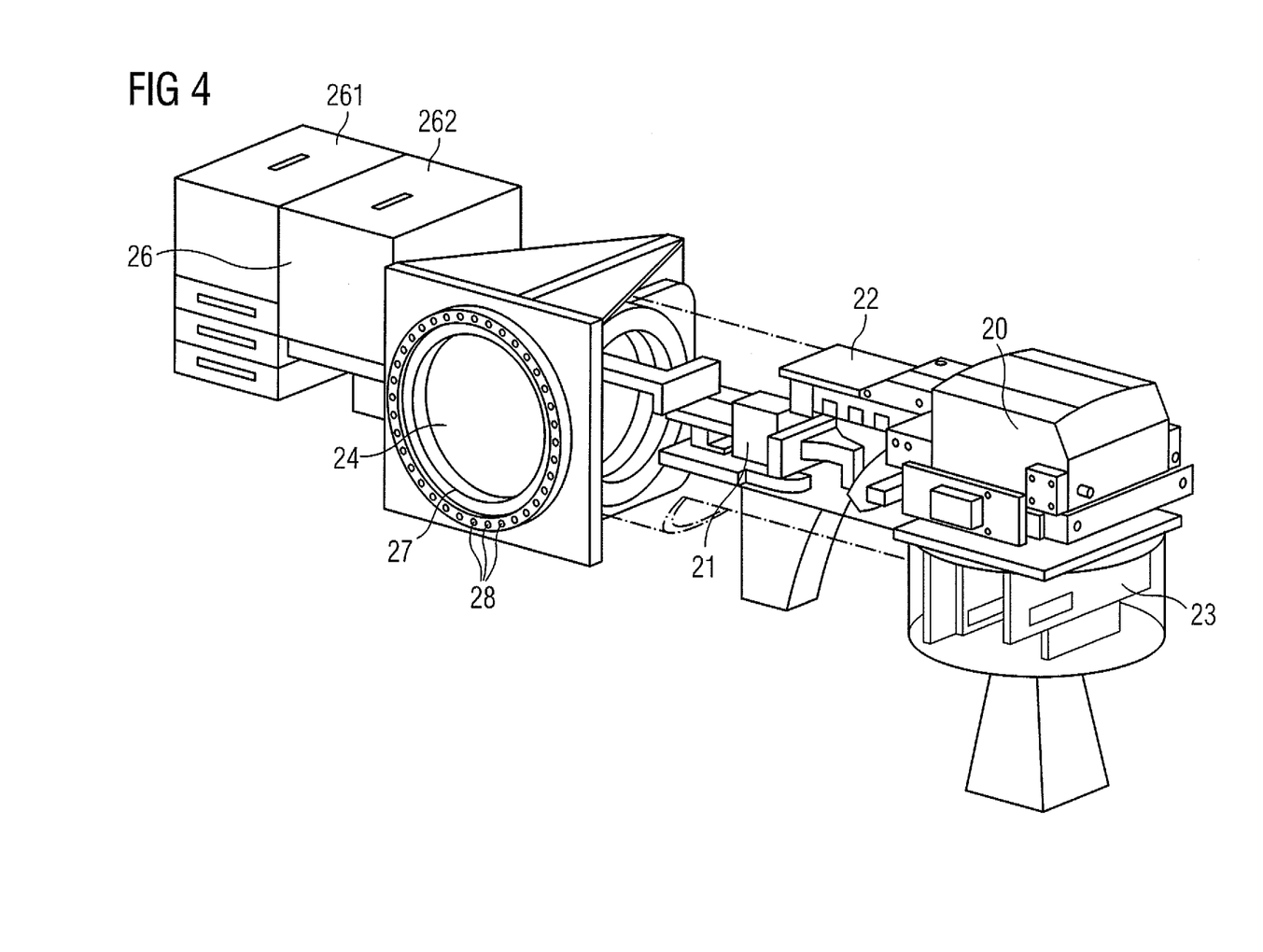
FIG. 4 shows a left-side view of one embodiment of an irradiator unit.

FIG. 4 shows one embodiment of an irradiator unit (e.g., a radiation unit). A beam deflector (e.g., a deflection magnet) and a target are contained at a head area 20 of the radiation unit. Accelerated electrons are shot at the target using a linear accelerator 22, so that X-ray radiation is produced. Collimation is provided downward through a multileaf collimator 23. The electrons come out of a high-voltage source (e.g., an injector) at approximately 15 kV and are shot into the linear accelerator 22 with a cathode 32 (e.g., an electron gun) (in FIG. 6).

The radiation unit also includes a mechanical interface 24, using which the radiation unit may be suspended or attached to a kinematic unit. This mechanical interface 24 is disposed in a central region of the radiation unit. "Central region" may be such that a ratio of the smaller to the larger of the distances in a direction of a longitudinal extension (e.g., direction 29 in FIG. 7) from ends of the radiation unit to a center of the mechanical interface 24 is, for example, ≥1/2 and maximally ≥1/3. Relevant paths for the determination of the ratio are designated in FIG. 6 by a and b (in the present case, because b<a, the ratio is b/a).

In a rear part of the radiation unit are a magnetron 25 (FIG. 5, FIG. 7) and components for energy generation and modulation 26. The components for energy generation and modulation 26 include, for example, a high-voltage modulator 262 and a high frequency (HF) power source 261. A circulator 21 is responsible for coupling out the reflected HF energy in a hollow conductor between the magnetron 25 and the linear accelerator 22. The mechanical interface 24 includes a ring 27, on which points 28 for attaching screws for a screw connection of the radiation unit are provided. The points 28 are provided along an entire circumference of the ring 27. Three of the points 28 are characterized, by way of example, with the reference character 28. The radiation unit is connected via the mechanical interface 24 to a system that provides degrees of freedom of movement for the radiation unit. These degrees of freedom of movement may include translations perpendicular to a direction, in which the radiation unit extends.

Figure 5:
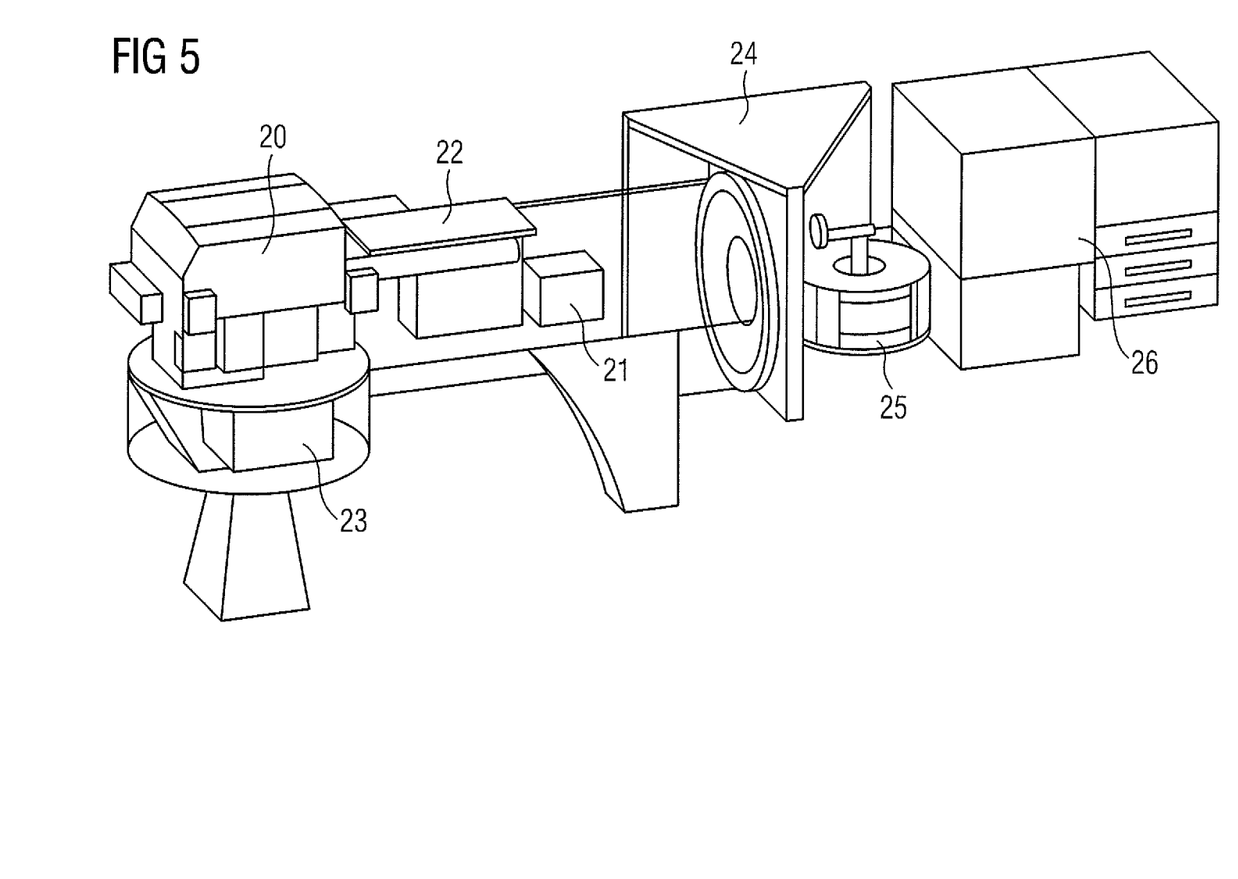
FIG. 5 shows a right-side view of one embodiment of an irradiator unit.
Figure 6:
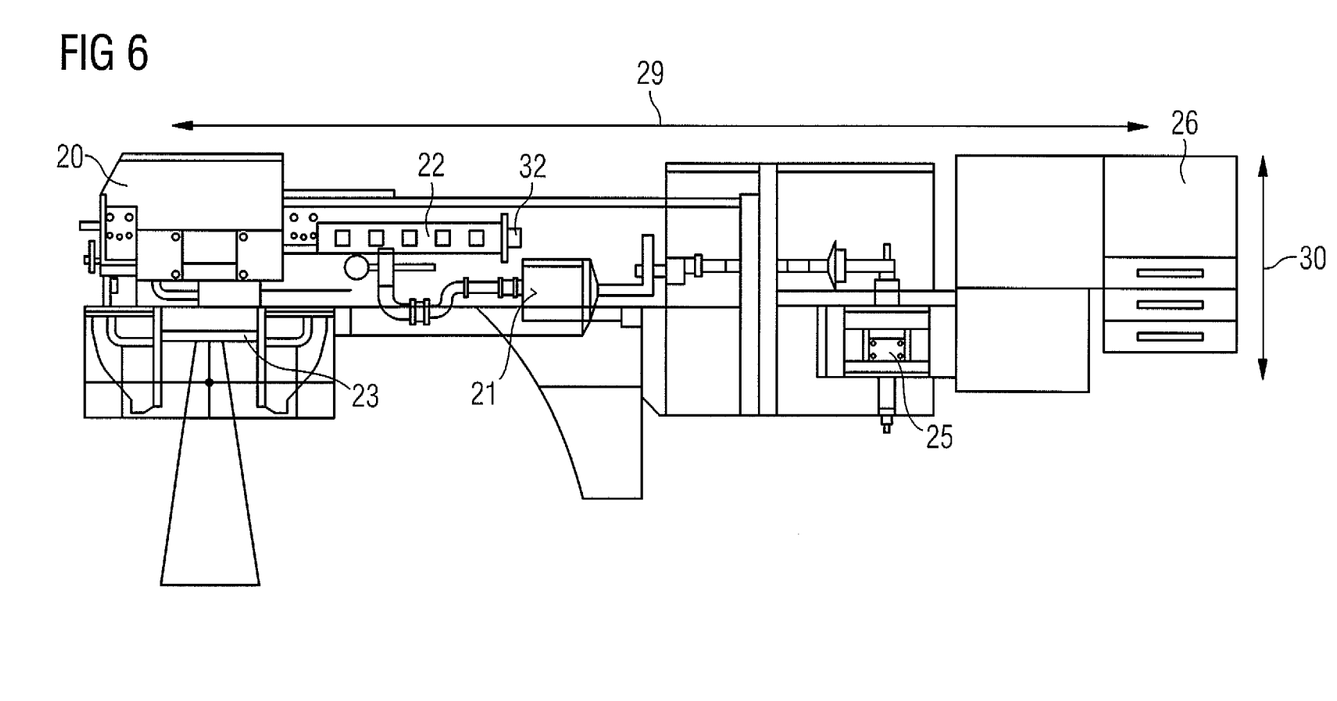
FIG. 6 shows a further side view of one embodiment of an irradiator unit.
Figure 7:
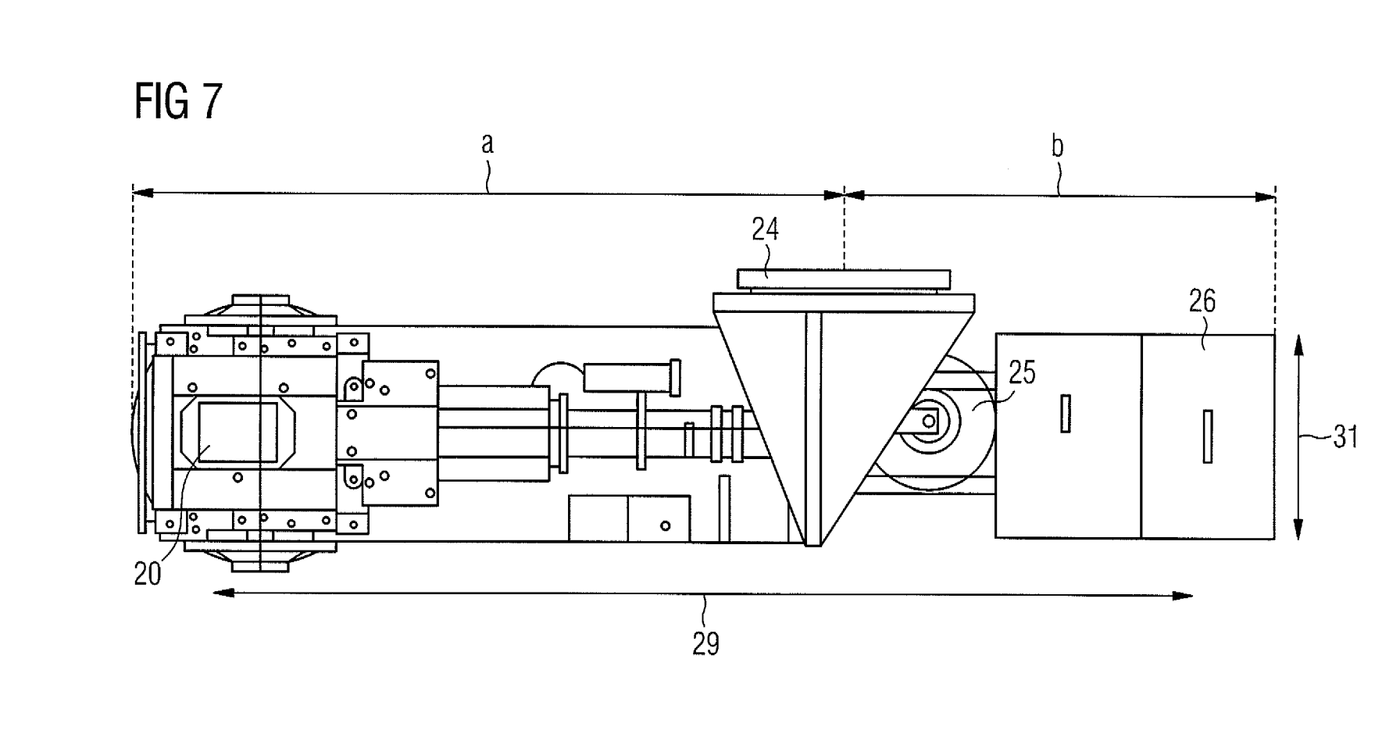
FIG. 7 shows a top view of one embodiment of an irradiator unit.

FIG. 5 to FIG. 7 show further views of one embodiment of the irradiator unit. FIG. 6 and FIG. 7 show an elongated, compact shape of the irradiator unit. The longitudinal extension is characterized by the reference character 29. In shape, the irradiator unit resembles a bar section that is several times longer in the longitudinal direction 29 than in the directions perpendicular thereto (e.g., vertical direction 30 and transverse direction 31). The average diameter in the vertical direction 30 is comparable to the transverse direction 31 is comparable (e.g., a difference of ≤1.5 and maximally ≤2). In contrast, the irradiator unit may extend in the longitudinal direction for many times (e.g., a factor of between 5 and 20) the average diameter in one of the other directions.

Figure 8:
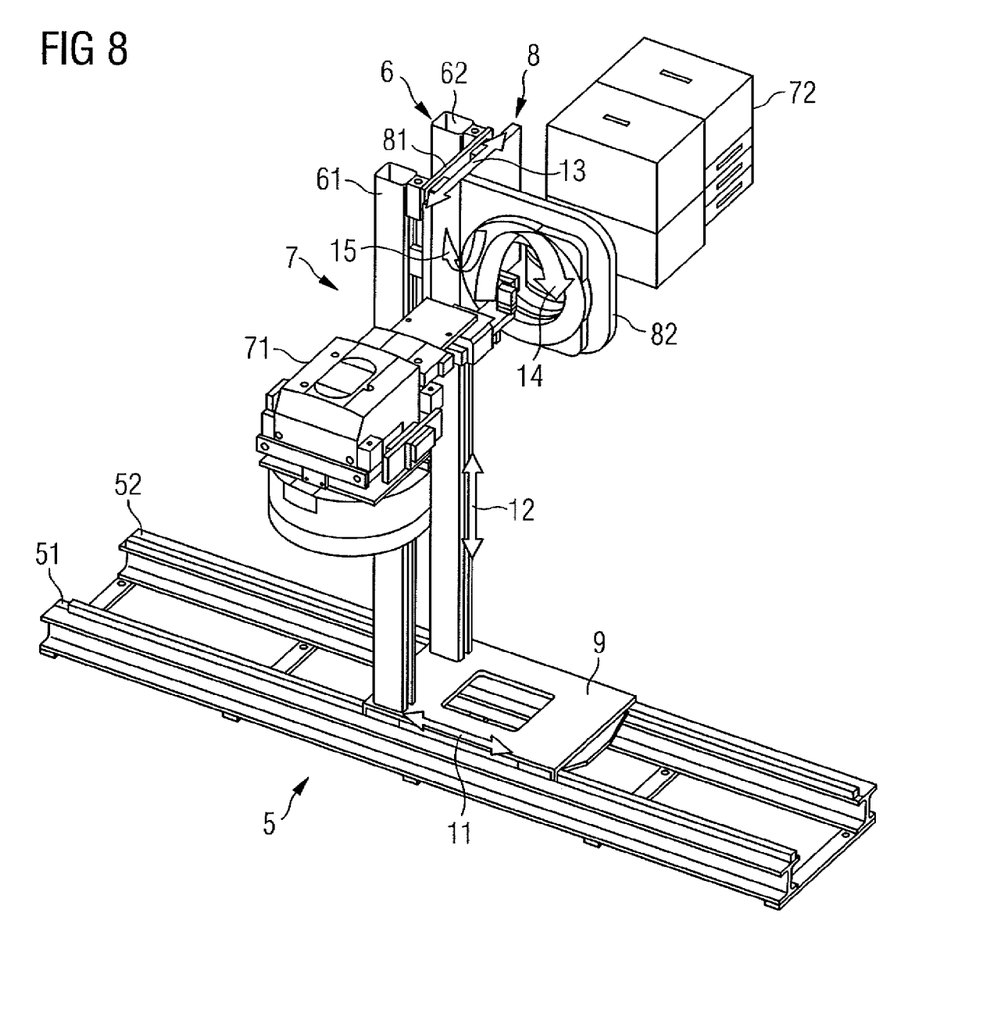
FIG. 8 shows an irradiation system with one embodiment of an irradiator unit.

FIG. 8 shows a kinematic unit with one embodiment of an irradiator unit (e.g., an irradiation apparatus). This is shown without casing (in contrast to FIGS. 1 and 2), in order better to understand the way the kinematic unit with the irradiator unit works. The whole apparatus rests on a floor guide 5. The floor guide is formed by two rails 51 and 52. Alternatively, a ceiling guide may be provided. A slide 9 is placed on the two rails 51 and 52 and supports the vertical guide 6. The vertical guide 6 is formed by two rails 61 and 62. A drive unit for the irradiation apparatus may be provided between the two rails 61 and 62 or on the slide 9. A support element 8 is provided for supporting the irradiator unit. The support element 8 may travel along the vertical guide 7. This is implemented in that the support element 8 is attached to a slide 81. A disk 82 having an opening is provided for feeding connections through between two parts 71 and 72 of the irradiator unit. The connections may be provided for the transmission of energy (e.g., cable) and for mechanical purposes (e.g., stability). The two parts 71 and 72 of the irradiator unit essentially serve different functions (e.g., energy generation (72) and radiation generation (71), respectively). The weight of the two components 71 and 72 of the irradiator unit is at least partially equalized with respect to the attachment location (e.g., designing the irradiator unit in essentially two parts reduces the stress such as the incidence of torques).

The system shown has five degrees of freedom. A degree of freedom of movement or translation along a horizontal axis 11 is provided. The degree of freedom of movement along the horizontal axis 11 is implemented using the slide 9. A translation in the vertical direction is implemented using the vertical guide 7 and the slide 81. Another degree of freedom is a translation along a transverse axis 13. This is, for example, implemented in that the disk 82 is able to move transversely on the slide 81. The irradiator unit may be rotated about an essentially transverse axis (e.g., degree of freedom 14). A degree of tilting freedom 15 that, in FIG. 3, exists with respect to a horizontal axis is provided.

All the degrees of freedom may, for example, interact such that an isocentric irradiation is obtained. For example, for this purpose, the degree of tilting freedom 15 and the transverse degree of freedom 13 may be jointly altered in a coordinated fashion.

The translational degrees of freedom for movement of the focus of the radiation source are implemented in that the entire irradiator unit completes the translational movements. The degrees of tilting and rotational freedom may be implemented both outside the irradiator unit as well as inside the irradiator unit. In the first instance, the entire irradiator unit may be rotated or tilted, and in the second instance, only a part (e.g., the head part) of the irradiator unit may be rotated or tilted.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation generation unit for a therapy system, the radiation generation unit comprising:
   a radiation source;
   support components for the radiation source, the support components comprising a power source;
   a stand comprising a horizontal guide, a vertical guide, a horizontal slide, a vertical slide, and a support element, the horizontal slide being positioned on the horizontal guide and supporting the vertical guide, the vertical slide being positioned on the vertical guide, the support element attached to the vertical guide and configured to travel along the vertical guide; and a mechanical interface, with which the power source is attachable to the stand at the support element, wherein the radiation source, the support components for the radiation source, and the mechanical interface form a linear, elongated structure, wherein the radiation generation unit comprises five degrees of freedom of movement, the five degrees of freedom of movement comprising:
  a first degree of freedom of movement along a horizontal axis using the horizontal slide,
  a second degree of freedom of movement along a vertical axis using the vertical slide,
  a third degree of freedom of movement along a transverse axis using the support element, wherein the transverse axis is perpendicular to the horizontal axis and extends through the linear, elongated structure,
  a fourth degree of freedom of movement rotating the linear, elongated structure about the transverse axis, and
  a fifth degree of freedom of movement tilting the linear, elongated structure at the mechanical interface.

2. The radiation generation unit as claimed in claim 1, wherein the mechanical interface is disposed in a central region of the linear, elongated structure.

3. The radiation generation unit as claimed in claim 2, wherein the mechanical interface includes a vertically oriented surface.

4. The radiation generation unit as claimed in claim 2, wherein the support components include a linear accelerator, a high frequency (HF) power source for the linear accelerator, a high-voltage supply for the HF power source, targets and filters for radiation, a dosimetry system for measuring generated radiation, collimators for beam formation, a power supply, control and monitoring electronics, a cooling apparatus, or a combination thereof.

5. The radiation generation unit as claimed in claim 2, wherein the radiation source and a linear accelerator are disposed in a front region of the radiation generation unit with respect to the linear, elongated structure, and wherein a power source for the linear accelerator and a high-voltage supply for the power source are disposed in a rear region of the radiation generation unit with respect to the linear, elongated structure.

6. The radiation generation unit as claimed in claim 1, wherein the mechanical interface includes a vertically oriented surface.

7. The radiation generation unit as claimed in claim 6, wherein the support components include a linear accelerator, a high frequency (HF) power source for the linear accelerator, a high-voltage supply for the HF power source, targets and filters for radiation, a dosimetry system for measuring generated radiation, collimators for beam formation, a power supply, control and monitoring electronics, a cooling apparatus, or a combination thereof.

8. The radiation generation unit as claimed in claim 1, wherein the support components include a linear accelerator, a high frequency (HF) power source for the linear accelerator, a high-voltage supply for the HF power source, targets and filters for radiation, a dosimetry system for measuring generated radiation, collimators for beam formation, a power supply, control and monitoring electronics, a cooling apparatus, or a combination thereof.

9. The radiation generation unit as claimed in claim 1, wherein the radiation source and a linear accelerator are disposed in a front region of the radiation generation unit with respect to the linear, elongated structure, and wherein a power source for the linear accelerator and a high-voltage supply for the power source are disposed in a rear region of the radiation generation unit with respect to the linear, elongated structure.

10. The radiation generation unit as claimed in claim 1, wherein the radiation generation unit extends in a longitudinal direction, and the longitudinal direction measures between 5 and 20 times of both an average diameter in a vertical direction and an average diameter in a transverse direction of the radiation generation unit, and wherein the vertical direction and the transverse direction are perpendicular to the longitudinal direction.

11. The radiation generation unit as claimed in claim 1, wherein the horizontal guide is a floor guide.

12. The radiation generation unit as claimed in claim 1, wherein the horizontal guide is a ceiling guide.

13. An irradiation apparatus comprising:
  a stand comprising a horizontal guide, a vertical guide, a horizontal slide, a vertical slide, and a support element, the horizontal slide being positioned on the horizontal guide and supporting the vertical guide, the vertical slide being positioned on the vertical guide, the support element attached to the vertical guide and configured to travel along the vertical guide; and
  a beam generation unit comprising:
    a radiation source;
    support components for the radiation source, the support components comprising a power source; and
    a mechanical interface, with which the power source is attachable to the stand at the support element,
  wherein the radiation source, the support components for the radiation source, and the mechanical interface form a linear, elongated structure,
  wherein the beam generation unit is demountably attached to the irradiation apparatus, and
  wherein the irradiation apparatus is configured to permit a movement of the beam generation unit along at least five degrees of freedom of movement,
  wherein a first degree of freedom of movement is a horizontal direction along the horizontal guide,
  wherein a second degree of freedom of movement is a vertical direction along the vertical guide, wherein the vertical direction is perpendicular to the horizontal direction,
  wherein a third degree of freedom of movement is a transverse direction along the support element, wherein the transverse direction is perpendicular to both the horizontal direction and the vertical direction,
  wherein a fourth degree of freedom of movement is a rotation of the beam generation unit along an axis in the transverse direction and extending through the beam generation unit, and
  wherein a fifth degree of freedom of movement is a tilt of the beam generation unit at the mechanical interface.

14. The irradiation apparatus as claimed in claim 13, wherein the support components include a linear accelerator, a high frequency (HF) power source for the linear accelerator, a high-voltage supply for the HF power source, targets and filters for radiation, a dosimetry system for measuring generated radiation, collimators for beam formation, a power supply, control and monitoring electronics, a cooling apparatus, or a combination thereof.

15. The irradiation apparatus as claimed in claim 13, wherein the mechanical interface is disposed in a central region of the linear, elongated structure.

16. An irradiation apparatus comprising:
a stand comprising a horizontal guide, a vertical guide, a horizontal slide, a vertical slide, and a support element, the horizontal slide being positioned on the horizontal guide and supporting the vertical guide, the vertical slide being positioned on the vertical guide, the support element attached to the vertical guide and configured to travel along the vertical guide; and
a beam generation unit comprising:
a radiation source;
support components for the radiation source, the support components comprising a power source; and
a mechanical interface, with which the power source is attachable to the stand at the support element,
wherein the beam generation unit is demountably attached to the irradiation apparatus, and
wherein the irradiation apparatus is configured to permit at least five degrees of freedom of movement of the beam generation unit,
wherein a first degree of freedom of movement is a horizontal direction along the horizontal guide,
wherein a second degree of freedom of movement is a vertical direction along the vertical guide, wherein the vertical direction is perpendicular to the horizontal direction,
wherein a third degree of freedom of movement is a transverse direction along the support element, wherein the transverse direction is perpendicular to both the horizontal direction and the vertical direction,
wherein a fourth degree of freedom of movement is a rotation of the beam generation unit along an axis in the transverse direction and extending through the beam generation unit, and
wherein a fifth degree of freedom of movement is a tilt of the beam generation unit at the mechanical interface.

17. The irradiation apparatus as claimed in claim 16, wherein the radiation source, the support components for the radiation source, and the mechanical interface form a linear, elongated structure.

18. The irradiation apparatus as claimed in claim 17, wherein the mechanical interface is disposed in a central region of the linear, elongated structure.

* * * * *